United States Patent [19]

Kuriyama

[11] Patent Number: 5,486,478
[45] Date of Patent: Jan. 23, 1996

[54] METHOD OF MEASURING INGREDIENTS IN LIQUID

[75] Inventor: Toshihide Kuriyama, Tokyo, Japan

[73] Assignee: NEC Corporation, Japan

[21] Appl. No.: 355,816

[22] Filed: Dec. 14, 1994

Related U.S. Application Data

[63] Continuation of Ser. No. 73,650, Jun. 7, 1993, abandoned, which is a continuation of Ser. No. 672,389, Mar. 20, 1991, abandoned.

[30] Foreign Application Priority Data

Mar. 23, 1990 [JP] Japan ...................... 2-72209

[51] Int. Cl.$^6$ .................................................. G01N 35/10
[52] U.S. Cl. .................. 436/52; 436/43; 436/95; 436/174; 436/179; 436/180; 422/63; 422/68.1; 422/81; 422/82; 422/100; 422/103; 73/863.73; 604/248
[58] Field of Search ................ 422/81, 82, 68.1, 422/67, 63, 99, 100, 103, 104; 436/43, 52, 53, 14, 174, 179, 180, 95; 73/863.71, 863.72, 863.73; 128/771; 604/246, 247, 248, 908

[56] References Cited

U.S. PATENT DOCUMENTS

| | | | |
|---|---|---|---|
| 3,306,111 | 2/1967 | Ferrin | 73/422 |
| 4,794,806 | 1/1989 | Nicoli et al. | 73/863.01 |
| 4,859,422 | 8/1989 | Qureshi et al. | 422/81 |
| 4,873,057 | 10/1989 | Robertson et al. | 422/75 |
| 4,920,056 | 4/1990 | Dasgupta | 422/81 |
| 4,920,060 | 4/1990 | Parrent, Jr. et al. | 436/178 |
| 4,946,795 | 8/1990 | Gibbons et al. | 436/179 |
| 4,980,130 | 12/1990 | Metzger et al. | 422/70 |
| 5,019,515 | 5/1991 | Gisin et al. | 436/52 |
| 5,200,051 | 4/1993 | Cozzette et al. | 204/403 |

*Primary Examiner*—James C. Housel
*Assistant Examiner*—Long V. Le
*Attorney, Agent, or Firm*—Laff, Whitesel, Conte & Saret, Ltd.

[57] ABSTRACT

A device for measuring the ingredients in liquid, primarily a body fluid. A valve has a reservoir composed of a communicating hole in the valve and a cell which is able to communicate with the reservoir. The cell may be connected with an inlet for a diluent through the reservoir and has a sensor and a stirrer. It is possible to measure the ingredients with accuracy and to realize a continuous monitoring thereof.

6 Claims, 2 Drawing Sheets

METHOD OF MEASURING INGREDIENTS IN LIQUID

This application is a continuation of application Ser. No. 08/073,650, filed Jun. 7, 1993, now abandoned, which was a continuation of Ser. No. 07/672,389, filed Mar. 20, 1991, now abandoned.

BACKGROUND OF THE INVENTION

1. Field of the Invention

This invention relates to a device for measuring ingredients in liquid and a method for measuring the same and more particularly to a device for measuring ingredients in a body fluid wherein the ingredients are measured by utilizing a very small amount of body fluid and a method for measuring the same.

2. Disclosure of the Prior Art

In the past, in order to analyze ingredients in body fluid by utilizing the body fluid, such as blood, an effusion fluid or the like, is obtained by vacuum-sucking skin from which a horny layer was removed. The body fluid was taken every measurement. It was set to an analytical instrument to measure the ingredients in the body fluid.

However, in this method, it is necessary to take the blood or effusion fluid with every measurement and to carry a sample to the analytical instrument. Thus, there have been defects, since the measurement becomes troublesome and the body fluid is taken with an amount more than that which is required to measure the ingredients. Specially, in the case where a change of the body fluid ingredients with time is monitored, the above defects have become a great problem because the defects cause pain and fluid consumption to the subject.

SUMMARY OF THE INVENTION

This invention was originated in order to obviate the above defects. It is an object of the invention to provide a method and a device for measuring ingredients in liquid with accuracy wherein it is possible to measure the ingredients in liquid by using a very small amount of a measuring sample and thus the ingredients in the body fluid are continuously and realizably monitored.

The above object is accomplished by a device for measuring ingredients in a liquid which comprises a valve established on a passage for taking the liquid to be measured, a reservoir for reserving a prescribed amount of the ingredients in liquid, which is composed of a communicating hole in the valve, and a cell which can be communicated to the reservoir by rotating the valve, said cell being able to be connected with a port for introducing a diluent through the reservoir and being provided with a sensor for detecting the ingredients in the liquid and a stirrer which are established in its interior.

The above object is also accomplished by a method for measuring ingredients in liquid which comprises the steps of:

connecting a communicating hole in a valve, which is established on a passage for taking the liquid to be measured, to a passage by which a port for introducing a diluent and a cell are joined and filling the cell with the diluent;

rotating the valve so as to connect the communicating hole in the valve to the passage for taking the liquid to be measured and filling the communicating hole with the liquid;

rotating the valve so an to connect the communicating hole in the valve to the passage, by which the introducing port of the diluent and the cell are joined, and pushing out the liquid within the communicating hole in the valve into the cell with the diluent;

measuring concentrations of ingredients in the liquid by a sensor for detecting the ingredients, while stirring the diluted liquid in the cell; and pouring the diluent into the cell and discharging the liquid out of the cell, the above steps being repeated in order.

BRIEF DESCRIPTION OF THE DRAWINGS

By way of example of the many features and advantages of the invention, illustrative embodiment in the device for measuring the ingredients in the liquid is described and shown in the accompanying drawings, in which.

DETAILED DESCRIPTION OF THE PREFERRED EMBODIMENT

According to this invention, there is obtained a device for measuring ingredients, such as urea and glucose, in such body fluid as an effusion fluid or the like which is obtained by vacuum-sucking the skin from which horny layer were removed.

This device is provided with a valve on a passage for taking the body fluid, a communicating hole in the valve being used as a reservoir for the body fluid. The body fluid with a specified amount is metered and taken due to rotation of the valve. Then, when the valve is communicated with the cell, a diluent having a constant pH and pH buffering ability and containing sufficient oxygen is introduced into the reservoir and herewith the body fluid of a specified amount in the reservoir is introduced into the cell together with the diluent. The cell is provided with a sensor for detecting ingredients, such as urea, glucose and the like, in the body fluid, on its inner wall, and a stirrer therein. Thus, by stirring the body fluid and diluent in the cell, the concentrations of ingredients in the body fluid diluted with a specified diluting degree, which is determined by a ratio of a volume of the communicating hole in the valve and an effective volume of the cell, are measured with accuracy by the prescribed sensor which was established on the inner wall of the cell.

In the device for measuring the ingredients in the liquid according to this invention, by using the diluent containing sufficient oxygen and having a specified pH, pH buffering ability and ionic strength, it is possible to control an oxygen concentration, pH and pH buffering ability of the diluted liquid to be measured. Also, in the case that there is used, as the sensor, a glucose sensor wherein a membrane on which glucose oxidase is immobilized is combined with an ion sensitive field-effect transistor (hereinafter referred to as ISFET) for detecting a change in pH, oxidation of glucose due to glucose oxidase is rapidly performed and thus it is possible to detect the pH change corresponding to the glucose concentrations by means of the ISFET and it is possible to improve accuracy in the measurement.

In addition, by repeating the steps as set forth in the above measurement, it is possible to measure semi-continuously the ingredients in the body fluid and thus to monitor the ingredients in the body fluid with its small amount.

EXAMPLE

Next, examples of this invention will be in detail described with reference to the accompanying drawings.

Figure 1:
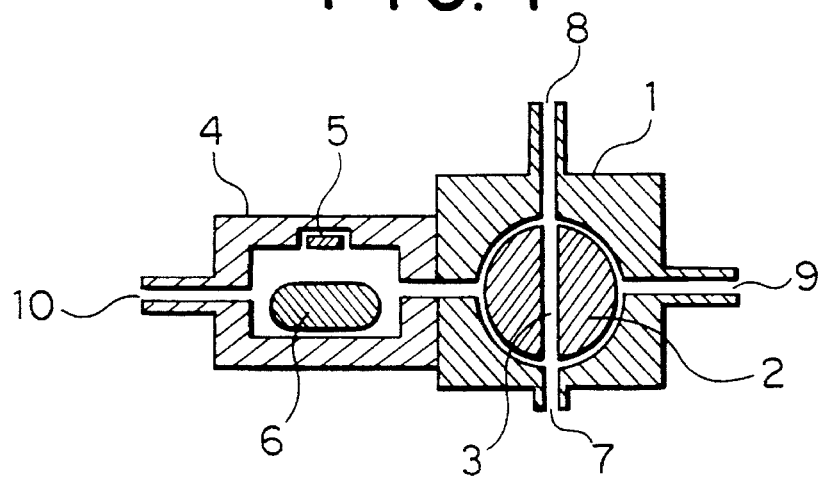
FIG. 1 shows a sectional view of one embodiment of the device for measuring the ingredients in the liquid according to this invention.

FIG. 1 shows a sectional view of one embodiment of the measuring device of the ingredients in the liquid according to this invention. In the drawing, a housing 1 has a valve 2 established on a passageway within said housing for taking ingredients in liquid, said passage running from an intake 7 of liquid to be measured to a suction port 8 of the liquid to be measured. In the valve 2, a communicating hole 3 was formed, doubling as a reservoir of the ingredients in the liquid and this communicating hole 3 can be connected to a port 9 for introducing a diluent and a cell 4 by rotating the valve 2. A stirrer 6 and a sensor 5 were established within the cell 4, said cell being provided with a discharge port 10.

FIG. 2 shows an explanation view illustrating an operating procedure of the above embodiment. Next, the procedure for measuring glucose concentrations in the body fluid, e.g. the effusion fluid, is described according to the device of the above embodiment. In FIG. 2, only the body fluid, the diluent and the diluted body fluid are hatched in order to make an illustration clear.

Figure 2A:
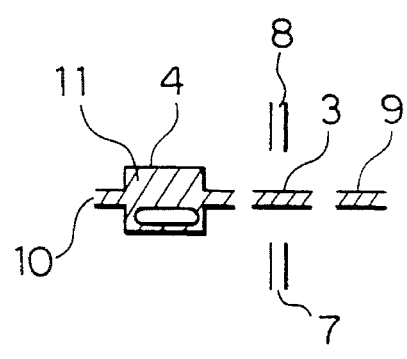
FIG. 2(a)–(d) shows an explanation view illustrating a procedure for taking an effusion fluid and measuring ingredients therein by using the device of FIG. 1.

First, in FIG. 2(a), the above valve was positioned in such that the communicating hole 3 was horizontal and the diluent 11, e.g. a 20 mM HEPES buffer at pH of 7.5, was introduced from the introducing port 9 for the diluent to fill the communicating hole 3 in the valve and the cell 4.

Figure 2B:
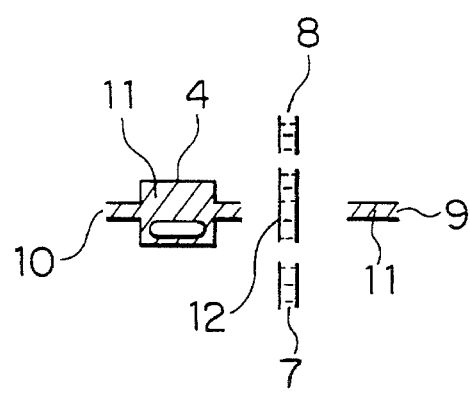

Then, as shown in FIG. 2(b), the valve was rotated in a 90-degree so that the communicating hole 3 in the valve was positioned on the passage for taking the ingredients in the liquid, by which the intake 7 of the liquid to be measured and the suction port 8 of the above liquid are joined, and the communicating hole 3 was filled with the body fluid 12.

Figure 2C:
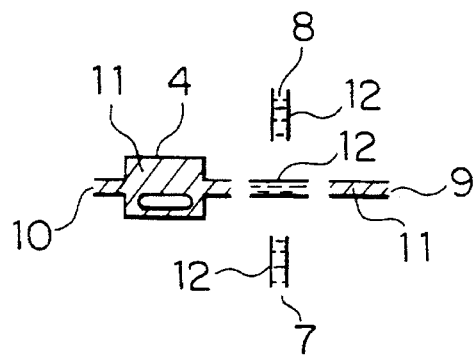
Figure 2D:
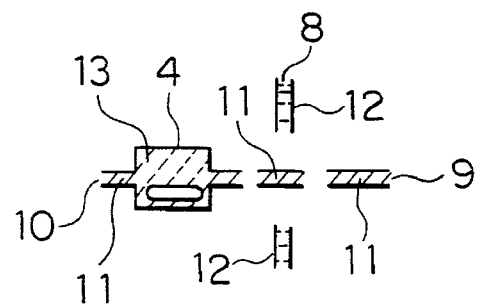

Moreover, as shown in FIG. 2(c), the valve was rotated in an additional 90-degree, the diluent 11 was fed from the introducing port 9 for the diluent and the body fluid 12 in the communicating hole 3 was pushed out into the cell 4 by the diluent 11. The body fluid 12 pushed out into the cell 4 was stirred by the stirrer 6 and diluted, and the glucose concentrations were measured by a glucose sensor established on the inner wall of the cell (FIG. 2(d)).

At this moment, a diluting degree of the body fluid was accurately determined on the basis of a ratio of the volume of the communicating hole 3 in the valve and the effective volume of the cell 4 and thus it becomes possible to dilute the body fluid with high accuracy. Generally, the pH and pH buffering ability of the body fluid are not constant. However, in the case that the pH buffer having a constant pH, pH buffering ability and ionic strength and having a sufficient oxygen concentration was used as the diluent, it becomes possible to control the pH, pH buffering ability, ionic strength and oxygen concentration of the sample to be measured and thus to perform a very accurate measurement.

For example, in the case that a suction cell having an inner diameter of 3 cm was connected to the intake 7 of liquid to be measured in order to collect the effusion fluid which was obtained by vacuum-sucking the skin from which horny layer was removed, the suction port of liquid to be measured was connected to a suction pump and about 400 Torr was kept, the effusion fluid was taken in an amount more than 1 µl per minute. When the volume of the communicating hole 3 was allowed to be 5 µl, the concentrations of glucose in the effusion fluid could be measured in about 5 minutes.

Figure 4:
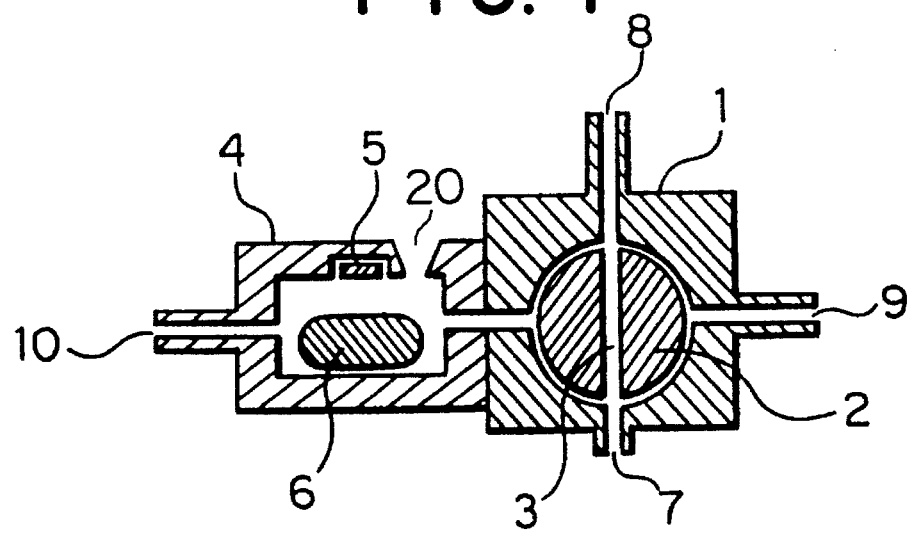
FIG. 4 shows an embodiment with a port into which a diluent may be poured.

Furthermore, by installing further a port 20 (FIG. 4) for pouring a washing diluent on the cell 4, the cell could be washed, while filling the communicating hole in the valve with the liquid to be measured and thus it was possible to shorten a measuring interval. In case of the above effusion fluid, it was possible to repeat the measurement of the glucose concentration every about 5 minutes.

Figure 3:
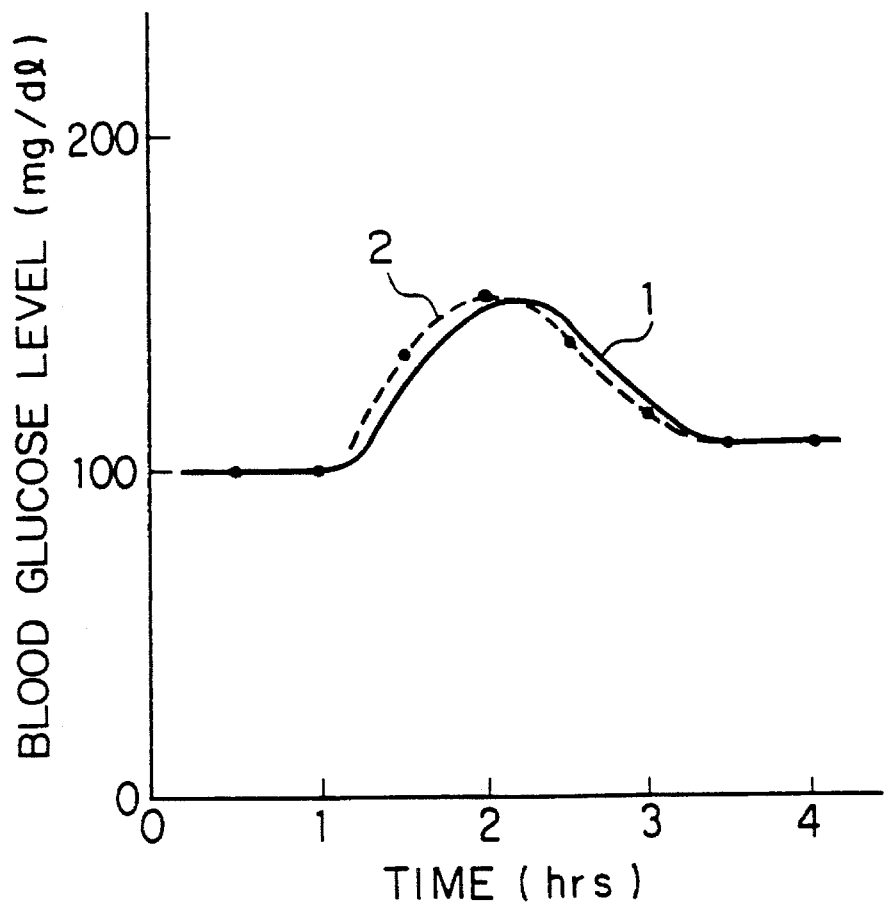
FIG. 3 shows a relationship between blood sugar levels (glucose concentration) which were continuously measured by using the device for measuring the ingredients in the liquid according to this invention and the measuring time.

Curve 1 as shown in FIG. 3 represents the result which was obtained by monitoring the glucose concentrations in the effusion fluid using the measuring device of the ingredients in the liquid according to this invention, i.e. the state of a change in the glucose concentrations during an oral glucose tolerance test. Curve 2 represents the state of a change in blood glucose levels (black dots) which were measured by taking the blood during the measurement. 75 g of glucose were taken 1 hour after starting the measurement. As can be seen from the drawing, the measurement using the effusion fluid exhibited a delay of about 10 minutes as compared with that of the blood but the both measurements showed a very good correlation.

In addition to the above embodiments, by establishing further a port being able to introduce a liquid containing known ingredients on the cell 4, it is possible to calibrate the sensor. In addition, the liquid as a measuring object is not limited to the effusion fluid and the blood and the measurement can apply to several liquids. Also, it is possible to select a kind of the sensor corresponding to the measuring object.

From the foregoing, it will be appreciated that, according to this invention, it is possible to provide the measuring device of the ingredients in the liquid which can measure the ingredient concentrations in the liquid with a very small amount with accuracy and realize continuous monitoring of the ingredients, and the measuring method of the same.

What is claimed is:

1. A method of measuring ingredients in a body fluid, said method comprising the steps of:

rotating a valve having a bore therein which forms a reservoir with a fixed volume for receiving a prescribed amount of said body fluid;

placing said bore in communication with an intake port and a suction port of a housing for taking said prescribed amount of said body fluid from said intake port and into the bore in said valve;

rotating said valve a second time to place said bore in communication with an introduction port for introducing a diluent into said bore and into a cell having a stirrer and a sensor therein, said cell having a discharge port, said second rotation of said valve occurring when said bore is filled with said prescribed amount of said body fluid;

transferring a sample of said prescribed amount of said body fluid from said bore and into said cell by a pressing force occurring with the introduction of said diluent into said bore;

diluting said prescribed amount of said body fluid with said diluent along with a stirring by said stirrer;

measuring a concentration of ingredients in said diluted body fluid by said sensor for detecting the ingredients, while said diluted body fluid is being stirred in said cell;

pouring a diluent into said cell through a port thereof and discharging said measured and diluted body fluid out of said cell; and repeating the above steps in the named order.

2. The method of measuring ingredients in a body fluid as defined in claim 1, wherein said cell is a suction cell.

3. The method of measuring glucose in a body fluid as defined in claim 1, wherein said body fluid is diluted with said diluent to a specific degree dilution which is determined by a ratio of a volume of said bore in the valve and an effective volume of said cell.

4. A method of measuring glucose in a body fluid, said method comprising the steps of:

rotating a valve having a bore therein which forms a reservoir with a fixed volume for receiving a prescribed amount of said body fluid;

placing said bore in communication with an intake port and a suction port of a housing for taking said prescribed amount of said body fluid from said intake port and into the bore in said valve;

rotating said valve a second time to place said bore in communication with an introduction port for introducing a HEPES buffer into said bore and into a cell having a stirrer and a glucose sensor therein, said cell having a discharge port, said second rotation of said valve occurring when said bore is filled with said prescribed amount of said body fluid;

transferring a sample of said prescribed amount of said body fluid from said bore and into said cell by a pressing force occurring with the introduction of said buffer into said bore;

diluting said prescribed amount of said body fluid with said buffer while stirring with said stirrer; and measuring a concentration of glucose in said diluted body fluid by said glucose sensor, while said diluted body fluid is being stirred in said cell;

pouring a diluent into said cell through a port thereof and discharging said diluted body fluid out of said cell; and repeating the above steps in the named order.

5. The method of measuring glucose in a body fluid as defined in claim 4, wherein said cell is a suction cell.

6. The method of measuring glucose in a body fluid as defined in claim 4, wherein said body fluid is diluted with said diluent to a specific degree of dilution which is determined by a ratio of a volume of said bore in the valve and an effective volume of said cell.

* * * * *